(12) United States Patent
Reynolds et al.

(10) Patent No.: US 8,511,310 B2
(45) Date of Patent: Aug. 20, 2013

(54) THERAPEUTIC MEDICAL APPLIANCE DELIVERY AND METHOD OF USE

(75) Inventors: Jason Reynolds, Charlotte, NV (US);
Tony D. Alexander, Charlotte, NC (US);
Ji Hwan You, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 451 days.

(21) Appl. No.: 12/819,969

(22) Filed: Jun. 21, 2010

(65) Prior Publication Data

US 2010/0305390 A1 Dec. 2, 2010

Related U.S. Application Data

(62) Division of application No. 10/567,508, filed as application No. PCT/US2004/025682 on Aug. 9, 2004, now Pat. No. 7,757,691.

(60) Provisional application No. 60/493,402, filed on Aug. 7, 2003.

(51) Int. Cl.
*A61M 16/00* (2006.01)
*A61F 2/06* (2006.01)

(52) U.S. Cl.
USPC ............. 128/207.15; 623/1.11; 623/1.3

(58) Field of Classification Search
USPC ............ 606/95, 157, 158, 213, 214; 623/1.1, 623/1.15, 1.16, 1.3, 1.31, 1.11; 128/831, 128/843, 207.15, 207.16; 424/422–424; 604/57, 58, 892.1
See application file for complete search history.

(56) References Cited

U.S. PATENT DOCUMENTS

| | | | |
|---|---|---|---|
| 3,196,876 | A | 7/1965 | Roberts et al. |
| 4,606,330 | A | 8/1986 | Bonnet |
| 4,795,434 | A | 1/1989 | Kujawaski |
| 4,893,623 | A | 1/1990 | Rosenbluth |
| 4,957,479 | A | 9/1990 | Roemer |

(Continued)

FOREIGN PATENT DOCUMENTS

| EP | 1036550 | 9/2000 |
|---|---|---|
| EP | 0137904 | 6/2003 |

OTHER PUBLICATIONS

European Examination Report dated Nov. 30, 2011 for EP04780509.8.

(Continued)

*Primary Examiner* — Julian Woo
(74) *Attorney, Agent, or Firm* — Stoel Rives LLP (57) ABSTRACT

The present invention, in an exemplary embodiment, provides a therapeutic medical appliance, delivery device and method of use. In particular, plug therapeutic medical appliances are provided that allow for the interventional treatment of pulmonary disorders such as defects characterized by pulmonary blebs and/or diffused destructive parenchymal disease. The plug therapeutic medical appliances themselves combine many of the excellent characteristics of both silicone and metal therapeutic medical appliances while eliminating the undesirable ones. In particular, these therapeutic medical appliances are preferably self-expanding in nature and allow the predetermined differential selection of relative hardness/softness of regions of the therapeutic medical appliance to provide additional patient comfort. An exemplary embodiment also provides a family of delivery devices that facilitate flexibility, durability and/or proper installation of one or more medical appliances in a single procedure. Moreover, the preferred embodiment of the delivery device provides for the reloading of the delivery device with additional medical appliances for additional interventional procedures.

31 Claims, 10 Drawing Sheets

(56) References Cited

U.S. PATENT DOCUMENTS

| | | | |
|---|---|---|---|
| 5,019,085 A | 5/1991 | Hillstead | |
| 5,159,920 A | 11/1992 | Condon et al. | |
| 5,223,265 A * | 6/1993 | Wong | 604/892.1 |
| 5,249,585 A | 10/1993 | Turner et al. | |
| 5,281,197 A * | 1/1994 | Arias et al. | 604/57 |
| 5,320,617 A | 6/1994 | Leach | |
| 5,409,453 A | 4/1995 | Lundquist et al. | |
| 5,503,635 A | 4/1996 | Sauer et al. | |
| 5,512,034 A | 4/1996 | Finn et al. | |
| 5,514,093 A | 5/1996 | Ellis et al. | |
| 5,549,644 A | 8/1996 | Lundquist et al. | |
| 5,588,949 A | 12/1996 | Taylor et al. | |
| 5,601,591 A | 2/1997 | Edwards et al. | |
| 5,603,698 A | 2/1997 | Roberts et al. | |
| 5,667,522 A | 9/1997 | Flomenblit et al. | |
| 5,697,971 A * | 12/1997 | Fischell et al. | 623/1.15 |
| 5,733,303 A * | 3/1998 | Israel et al. | 623/1.15 |
| 5,735,859 A | 4/1998 | Fischell et al. | |
| 5,746,692 A | 5/1998 | Bacich et al. | |
| 5,782,807 A | 7/1998 | Flavai et al. | |
| 5,782,838 A | 7/1998 | Beyar et al. | |
| 5,817,102 A | 10/1998 | Johnson et al. | |
| 5,824,058 A | 10/1998 | Ravenscroft et al. | |
| 5,833,694 A | 11/1998 | Poncet | |
| 5,843,158 A * | 12/1998 | Lenker et al. | 623/1.13 |
| 5,902,333 A | 5/1999 | Roberts et al. | |
| 5,904,693 A | 5/1999 | Dicesare et al. | |
| 5,984,964 A | 11/1999 | Roberts et al. | |
| 6,019,778 A | 2/2000 | Wilson et al. | |
| 6,086,528 A | 7/2000 | Adair | |
| 6,162,231 A | 12/2000 | Milcus et al. | |
| 6,302,906 B1 | 10/2001 | Goicoechea et al. | |
| 6,322,586 B1 | 11/2001 | Monroe et al. | |
| 6,325,790 B1 | 12/2001 | Trotta | |
| 6,352,541 B1 | 3/2002 | Kienzle | |
| 6,369,355 B1 | 4/2002 | Saunders | |
| 6,375,676 B1 | 4/2002 | Cox | |
| 6,416,545 B1 | 7/2002 | Mikus et al. | |
| 6,451,025 B1 | 9/2002 | Jervis | |
| 6,494,908 B1 | 12/2002 | Huxel et al. | |
| 6,517,569 B2 | 2/2003 | Mikus et al. | |
| 6,569,085 B2 | 5/2003 | Kortenbach et al. | |
| 6,599,314 B2 | 7/2003 | Mathis | |
| 6,616,689 B1 * | 9/2003 | Ainsworth et al. | 623/1.16 |
| 6,623,491 B2 | 9/2003 | Thompson | |
| 6,626,902 B1 | 9/2003 | Kucharczyk et al. | |
| 6,656,211 B1 | 12/2003 | DiCaprio | |
| 6,656,214 B1 | 12/2003 | Fogarty et al. | |
| 6,663,660 B2 | 12/2003 | Dusbabek et al. | |
| 6,663,880 B1 | 12/2003 | Roorda et al. | |
| 6,669,716 B1 | 12/2003 | Gilson et al. | |
| 6,669,718 B2 | 12/2003 | Besselink | |
| 6,669,720 B1 | 12/2003 | Pierce | |
| 6,673,101 B1 | 1/2004 | Fitzgerald et al. | |
| 6,676,692 B2 | 1/2004 | Rabkin et al. | |
| 6,676,693 B1 | 1/2004 | Belding et al. | |
| 6,689,157 B2 | 2/2004 | Madrid et al. | |
| 6,695,809 B1 | 2/2004 | Lee | |
| 6,695,812 B2 | 2/2004 | Estrada et al. | |
| 6,695,862 B2 | 2/2004 | Cox et al. | |
| 6,699,274 B2 | 3/2004 | Stinson | |
| 6,699,277 B1 | 3/2004 | Freidberg et al. | |
| 6,702,849 B1 | 3/2004 | Dutta et al. | |
| 6,702,850 B1 | 3/2004 | Byun et al. | |
| 6,723,071 B2 | 4/2004 | Gerdts et al. | |
| 6,723,113 B1 | 4/2004 | Shkolnik | |
| 6,726,712 B1 | 4/2004 | Raeder-Devens et al. | |
| 6,733,521 B2 | 5/2004 | Chobotov et al. | |
| 6,736,828 B1 | 5/2004 | Adams et al. | |
| 6,743,219 B1 | 6/2004 | Dwyer et al. | |
| 6,746,423 B1 | 6/2004 | Wantink | |
| 6,749,627 B2 | 6/2004 | Thompson et al. | |
| 6,749,628 B1 * | 6/2004 | Callol et al. | 623/1.15 |
| 6,752,819 B1 | 6/2004 | Brady et al. | |
| 6,752,825 B2 | 6/2004 | Eskuri | |
| 6,755,855 B2 | 6/2004 | Yurek et al. | |
| 6,761,703 B2 | 7/2004 | Miller et al. | |
| 6,761,708 B1 | 7/2004 | Chiu et al. | |
| 6,761,733 B2 | 7/2004 | Chobotov et al. | |
| 6,773,446 B1 | 8/2004 | Dwyer et al. | |
| 6,773,447 B2 | 8/2004 | Laguna | |
| 6,773,448 B2 | 8/2004 | Kusleika et al. | |
| 6,780,182 B2 | 8/2004 | Bowman et al. | |
| 6,780,199 B2 | 8/2004 | Solar et al. | |
| 6,790,220 B2 | 9/2004 | Morris et al. | |
| 6,790,223 B2 | 9/2004 | Reever | |
| 6,800,081 B2 | 10/2004 | Parodi | |
| 6,802,846 B2 | 10/2004 | Hauschild et al. | |
| 6,802,849 B2 | 10/2004 | Blaeser et al. | |
| 6,808,529 B2 | 10/2004 | Fulkerson | |
| 6,997,918 B2 * | 2/2006 | Soltesz et al. | 128/207.16 |
| 7,137,993 B2 | 11/2006 | Acosta et al. | |
| 7,547,321 B2 * | 6/2009 | Silvestri et al. | 623/1.15 |
| 7,594,927 B2 * | 9/2009 | Majercak et al. | 623/1.15 |
| 7,757,691 B2 | 7/2010 | Reynolds et al. | |
| 2002/0161425 A1 | 10/2002 | Hemerick et al. | |
| 2002/0183763 A1 | 12/2002 | Callot et al. | |
| 2002/0198593 A1 | 12/2002 | Gomez et al. | |
| 2003/0144671 A1 | 7/2003 | Brooks et al. | |
| 2004/0088040 A1 | 5/2004 | Mangiardi et al. | |
| 2004/0193243 A1 | 9/2004 | Mangiardi et al. | |

OTHER PUBLICATIONS

International Search Report for PCT/US2004/025682 dated Aug. 18, 2005.

Written Opinion of the International Searching Authority from PCT/US2004/025682 dated Jul. 6, 2005.

Notice of Allowance and Fees due for U.S. Appl. No. 10/567,508 dated Mar. 9, 2010.

\* cited by examiner

THERAPEUTIC MEDICAL APPLIANCE DELIVERY AND METHOD OF USE

CROSS-REFERENCE TO RELATED APPLICATIONS

This patent application is a divisional of U.S. patent application Ser. No. 10/567,508, now U.S. Pat. No. 7,757,691, entitled THERAPEUTIC MEDICAL APPLIANCE DELIVERY AND METHOD OF USE, which is a national phase filing of International Application No. PCT/US04/25682, filed on Aug. 9, 2004, which claims priority from U.S. Provisional Patent Application No. 60/493,402, filed on Aug. 7, 2003, all of which are fully incorporated by reference herein.

FIELD OF INVENTION

The present invention relates generally to medical devices directed to interventional treatment, and more particularly to plugs, delivery devices and methods for utilizing these plugs in the treatment of pulmonary disorders such as defects characterized by pulmonary blebs and/or diffused destructive parenchymal disease.

BACKGROUND OF THE INVENTION

Therapeutic medical appliances are devices that are inserted into a vessel or passage to keep the lumen open and prevent closure due to a stricture, external compression, or internal obstruction. In particular, therapeutic medical appliances are commonly used to keep blood vessels open in the coronary arteries and they are frequently inserted into the ureters to maintain drainage from the kidneys, the bile duct for pancreatic cancer or cholangiocarcinoma or the esophagus for strictures or cancer. Vascular as well as not vascular therapeutic medical applianceing has evolved significantly; unfortunately there remain significant limitations with respect to the technology for producing therapeutic medical appliances suitable to various portions of a patient's anatomy.

Unfortunately, because of the topology of the human lungs generally and the various lobes in particular, traditional therapeutic medical applianceing is not effective in the treatment of pulmonary blebs and/or diffused destructive parenchymal disease. In most cases, attempts are made to section off lung tissue, which generally results in fluid retention and concomitant complications. Even if there was a way to deliver a therapeutic medical appliance to one bleb, it would require multiple procedures to address the common presence of multiple blebs.

Physicians have attempted to improve lung function in patients with emphysema by utilizing lung volume reduction procedures. The principal behind such procedures is that if the increased residual volume created by the bullous of disease could be reduced, the patients' respiratory limitations could be alleviated. Lung volume reduction procedures are very invasive and are only available to a minority of emphysema patients and require significant post surgical care and rehabilitation. Alternative systems have attempted to install valve systems that allow for the alleviation of respiratory limitations by closing blebs without the undesirable back filling of the closed areas. Regrettably, the valve system has a relatively short useful life, and therefore limited applicability, since patients with emphysema also have chronic bronchitis and thus lots of secretions in their airways to obstruct the valves. Moreover, placement of these valves requires invasive procedures as well.

Therefore there remains a need for a therapeutic medical appliance that can be placed in the segmental airways so as to reduce the residual volume and improve ventilation in a less invasive manner. Chiefly, there remains an existing need for a device and delivery method for installing the device in the lungs of a patient to treat pulmonary blebs or other suitable abnormalities. In particular, there is a need for a specialized therapeutic medical appliance designed to plug fissures or other abnormal anatomical openings. Moreover, there is an existing need for an interventional technique that allows for the delivery of multiple therapeutic medical appliances during a single procedure, without having to remove the delivery device. A need also remains for a delivery device that can be reloaded with a plurality of therapeutic medical appliances. There also remains a need for a method of treating pulmonary blebs that prevents disease recurrence in, aggravation and/or deterioration of the patient's pulmonary health.

SUMMARY OF EXEMPLARY EMBODIMENTS

It is a principal purpose of the present invention to provide a specialized medical appliance, in accordance with an exemplary embodiment of the present invention, which can be indicated for a number of disorders, including particularly the treatment of pulmonary disorders such as defects characterized diffused destructive parenchymal disease. In particular, it is an objective of a preferred embodiment in accordance with the present invention to provide a medical appliance that is easily installed, yet in alternative embodiments, removable. Moreover the medical appliance in accordance with this embodiment of the present invention would not cause material infections and may be capable of reducing infection. Therefore, a principal objective of a preferred embodiment in accordance with the present invention is to provide a prosthesis that is suitable for both permanent and temporary use while being easy to insert, reposition and remove.

A principal objective of a preferred embodiment of the present invention is to provide a medical appliance that may be stamped from preferably a single material that is capable of maintaining its axial working length when radially compressed. To this end, the therapeutic medical appliance does not have a seam that could aggravate luminal tissue. In particular, a medical appliance in accordance with the present invention is formed using a tool that molds the medical appliance's outer contour as well as its interstices.

It is yet another objective of an exemplary embodiment of the present invention to provide a medical appliance that can be indicated for the treatment of pulmonary blebs and improve the way clinicians treat malignant obstructions.

Still another objective of the present invention is to provide a medical appliance and method for installing the medical appliance that is economical and suitable for routine purposes. Moreover, a preferred embodiment of the medical appliance has a self-sealing membrane at one or both end to allow for the closing off of the target area while allowing the physician to introduce and/or evacuate material there through.

A principal objective of an exemplary therapeutic medical appliance in accordance with the present invention is to provide a family of medical appliances where the relative hardness/softness of regions of the therapeutic medical appliance can differ from other regions of the therapeutic medical appliance to provide additional patient comfort and resistance to radial forces.

An additional objective in accordance with an exemplary embodiment is to provide a family of medical appliances with novel interstice configurations that facilitate flexibility, durability and/or proper installation.

Yet another principal objective of an exemplary delivery system in accordance with the present invention to provide a device that can facilitate the precise delivery of the medical appliances in a safe and repeatable fashion. In the furtherance of this and other objectives, a preferred deployment apparatus allows the physician to concentrate on correct placement without having to estimate extent of deployment. In particular, in a preferred embodiment, the present device has a physical safety mechanism that limits deployment to the critical deployment point (i.e., ~60%). The critical deployment point may range from 5% to 95% but is preferably about 60%. At this point, if the physician is satisfied with placement, she can engage the safety means to what we refer to as the Proceed Orientation (PO) and fully deploy the medical appliance. It is preferred that when the safety mechanism is engaged to the PO, a tactile, visual and/or possible audible indicator sounds to inform the physician that if she deploys the therapeutic medical appliance any further, she can no longer retract the therapeutic medical appliance beyond this point. Though the present therapeutic medical appliance and delivery system eliminates the need for repositioning, such safety features are still preferable. In a preferred embodiment, the slight audible indication is the sound of a tab or stop snapping to allow free deployment of the therapeutic medical appliance.

Still another objective of an exemplary embodiment in accordance with the present invention is to provide a delivery system that allows for the placement of multiple medical appliances during a single procedure without having to first remove the delivery device. Moreover, the delivery device in alternative embodiments may be reloaded by attaching removable medical appliance containing housings thereto.

An additional objective in accordance with an alternative embodiment of the present invention is to provide a delivery system that has an outer tubular member of sufficient cross sectional thickness to define a plurality of longitudinally extending channels for receiving additional utility tools. In the furtherance of this and other objectives, and by way of example only, one such channel could accommodate an ultra thin scope while an alternative channel receives a guidewire, syringe systems, etc. Principally, these channels are suitable for receiving a number of other tools that a physician may need during deployment of a therapeutic medical appliance or therapeutic treatment of target tissue.

Still another objective in accordance with a preferred embodiment of the present invention is to provide a device having direct visualization capabilities directly incorporated into the device.

In addition to the above objectives, an exemplary deployment system preferably has one or more of the following characteristics: (1) biocompatible; (2) compliant with specialized radially expanding plug medical appliances; (3) capable of distal or proximal medical appliance release; (4) smooth and clean outer surface; (5) length of the device variable according to the insertion procedure to be employed; (6) outer dimension as small as possible (depends on the diameter of crimped medical appliance); (7) dimensions of the device must offer enough space for the crimped medical appliance; (8) sufficient flexibility to adapt to anatomical curvatures without loss of ability to push or pull; (9) low friction between the moving parts; (10) sufficient resistance to kinking; (11) good deployment force, ability to reposition partially deployed medical appliance; and (12) sufficiently economical to manufacture so as to make the deployment apparatus disposable.

Further objectives, features and advantages of the invention will be apparent from the following detailed description taken in conjunction with the accompanying drawings.

DETAILED DESCRIPTION OF AN EMBODIMENT

The present invention, in a preferred embodiment, provides a therapeutic medical appliance, the delivery system, and method of using the appliance and delivery system for the treatment of abnormalities, defined by fissures or other openings in the tissue, that require the closing or sealing off of the abnormalities. In particular, the present medical appliance is designed to treat pulmonary blebs and/or diffused destructive parenchymal disease in a patient. To this end, preferred delivery systems allow the user to install the multiple therapeutic medical appliances in various target sites in the segmental airway during a single procedure. In alternative embodiments, the delivery system may be reloadable with one or more additional therapeutic medical appliances.

A preferred therapeutic medical appliance is preferably formed from a composite material selected from the group consisting essentially of Ni, C, Co, Cu, Cr, H, Fe, Nb, O, Ti, plastic, other polymers in general and bioabsorbable polymers, in particular, and combinations thereof. However, alternative materials such as polymeric material, is acceptable provided that the therapeutic medical appliance has radial self-expansion ability. Making specific reference to the memory metal embodiments, the composite material is generally formed into a compressed tube from which the therapeutic medical appliance is etched and is formed on a suitable shaping device to give the therapeutic medical appliance the desired external geometry. Both the synthetic collar techniques and in vitro valuation techniques show the remarkable ability of therapeutic medical appliances in accordance with the present invention to convert acting force into deformation work absorbed by the angled structure, which prevents excessive scaffolding stress and premature material fatigue and accelerated obsolescence.

Though one skilled in the therapeutic medical appliance engineering art, once apprised of the present application, would be able to manufacture a therapeutic medical appliance consistent with the present invention by other methods, a preferred method of manufacturing such therapeutic medical appliances follows. As stated above a composite material is selected and a blank is formed there from. The blank is preferably loser etched and the etch work is generally verified for accuracy using visual recording microscopy. Dimensional measurements are taken to ensure strut thickness, segment angles, zone placement, etc. Moreover, the therapeutic medical appliance is preferably formed on a shaping tool that has substantially the desired contour of the external therapeutic medical appliance dimensions. A coating may be coupled with the scaffolding. The coating may be of sufficient thickness to prevent the medical appliance from becoming epithelialized when installed in the desired portion of the patient's anatomy. The coating may be configured to not inhibit flexing or radial expansion of the medical appliance. The coating may be coupled with the medical appliance about the first and second ends thereof. Anti-microbial agents and/or chemotherapeutic agents may be coupled with the medical appliance.

In the event the therapeutic medical appliance is to be shaped to the dimensions of a particular lumen, optical photography and/or optical videography of the target lumen may be conducted prior to therapeutic medical appliance formation. Alternatively, an appliance sizing device like the Lumenaide™ designed by Alveolus Inc may be used. The geometry of corresponding zones and connector regions of the therapeutic medical appliance then can be etched and formed in accordance with the requirements of that target lumen.

It should be pointed out that unlike the use of differing shape memory materials to change regions of a therapeutic medical appliance, therapeutic medical appliances in accordance with the present invention can take on an infinite number of characteristic combinations as zones and segments within a zone can be modified by changing angles, segment lengths and segment thicknesses during the etching and forming stages of therapeutic medical appliance engineering or during post formation processing and polishing steps. Moreover, by modifying the geometry of the connectors between zones, addition functionality may be achieved.

Exemplary therapeutic medical appliances in accordance with the present invention may be manufactured for particular lumen in accordance with the manufacturing procedures and containing the characteristics of the devices disclosed in patent application Ser. No. 10,288,615, which has been incorporated in its entirety by this reference.

The therapeutic medical appliance is preferably formed of memory metal and preferably has unique geometrical interstices that are laser etched therein. However, other conventional ways of forming interstices in unitary therapeutic medical appliances, though not equivalent are contemplated and may be employed and would be within the skill set of one in the art.

It cannot be overemphasized, however, that this does not mean the knowledge that changes in the geometry of interstices affect therapeutic medical appliance functionality is currently known in the art. To the contrary, the present inventors discovered the interrelation between interstice geometry, width, length and relative resistance to torsional stress and radial force. In fact, it can be said that the therapeutic medical appliance has circumferential bands extending perpendicularly with respect to the luminal device's longitudinal axis. These bands are referred to generally as zones. A connector connects these bands to one another; the connector is an additional means for adjusting therapeutic medical appliance functionality. In particular, the connector defines a substantially U shaped member, but could define other geometries such as U, V, W, Z, S and X to name a few.

With specific reference being made to a preferred embodiment of the present invention, a therapeutic medical appliance is provided for introduction into a cavity in the anatomy of a patient, the medical appliance comprising a tube with first and second ends and the tube defining a cavity extending between the first and second ends, the medical appliance further comprising a self-sealing membrane coupled about the first end thereof. Preferred self-sealing membrane materials include but are not limited to polymers such as thin rubber.

In the instance where the target location of the therapeutic medical appliance(s) is the lungs, multiple appliances may be needed in order to treat the patient. Unfortunately, heretofore there was no appliance suitable for such treatment, nor was there a device that allows the installation of multiple appliances during a single moderately invasive procedure. A preferred device comprises a longitudinally extending outer tubular member having distal and proximal ends and an interior and exterior surface, the outer tubular member defines a lumen longitudinally extending substantially the distance from the distal end to the proximal end of the outer tubular member and forming a longitudinal expanse there between, running parallel to the longitudinal expanse are a plurality of grooves, the longitudinal expanse forming a lumen there through; a plurality of tracks complementary and slidably coupled with the grooves such that the tracks and the grooves linearly displaceable with respect to the other, the tracks having proximal and distal ends and a plurality of tabs spaced at a functional distance apart from one another between the proximal and distal ends thereof, the tabs facing toward the lumen of the outer tubular member; and a handle, coupled with a portion of the outer tubular member, the handle having first and second ends. The handle cooperates with the tracks in a manner consistent with reliable and deliberate delivery of each therapeutic medical appliance. In alternative embodiments, the delivery device comprises a safety system like the one provided in U.S. patent application Ser. No. 10/404,197, which is incorporated in its entirety by this reference. With respect to the safety mechanism, a preferred mechanism is a physical safety mechanism that limits deployment to the critical deployment point (i.e., ~60%). The critical deployment point may range from 5% to 95% but is preferably about 60% or a proportional stop relative to the stent length. At this point, if the physician is satisfied with placement, she can engage the safety means to what we refer to as the Proceed Orientation (PO) and fully deploy the therapeutic medical appliance. It is preferred that when the safety mechanism is engaged to the PO, a sensation or possible audible indicator sounds to inform the physician that if she deploys the therapeutic medical appliance any further, she can no longer retract the delivery system beyond this point and still reposition the therapeutic medical appliance. Certain embodiments (not shown) provide for re-constrainment beyond this point. In addition to or as an alternative, the tabs on the tracks also serve as a safety function to prevent deployment of more than one appliance at a time while also facilitating reloading. Though the present stent and delivery system eliminates the need for repositioning, such safety features are still preferable. In a preferred embodiment, the slight audible indication is the sound of a tab or stop snapping or being traversed to allow free deployment of the appliance. The therapeutic medical appliance may also have seating barbs for retention.

The distal end of the device may be configured such that a portion of the distal region is removable, preferably including the distal portions of the tracks such that a housing containing additional therapeutic medical appliances can be coupled with the device to form a reloadable delivery device. Alternatively, the device may be reloaded with a single appliance containing distal tip, which can be screwed onto the device or coupled with the device by other conventional means.

Making specific reference to the FIGS, a therapeutic medical appliance and delivery device are provided in various embodiments.

Figure 1:
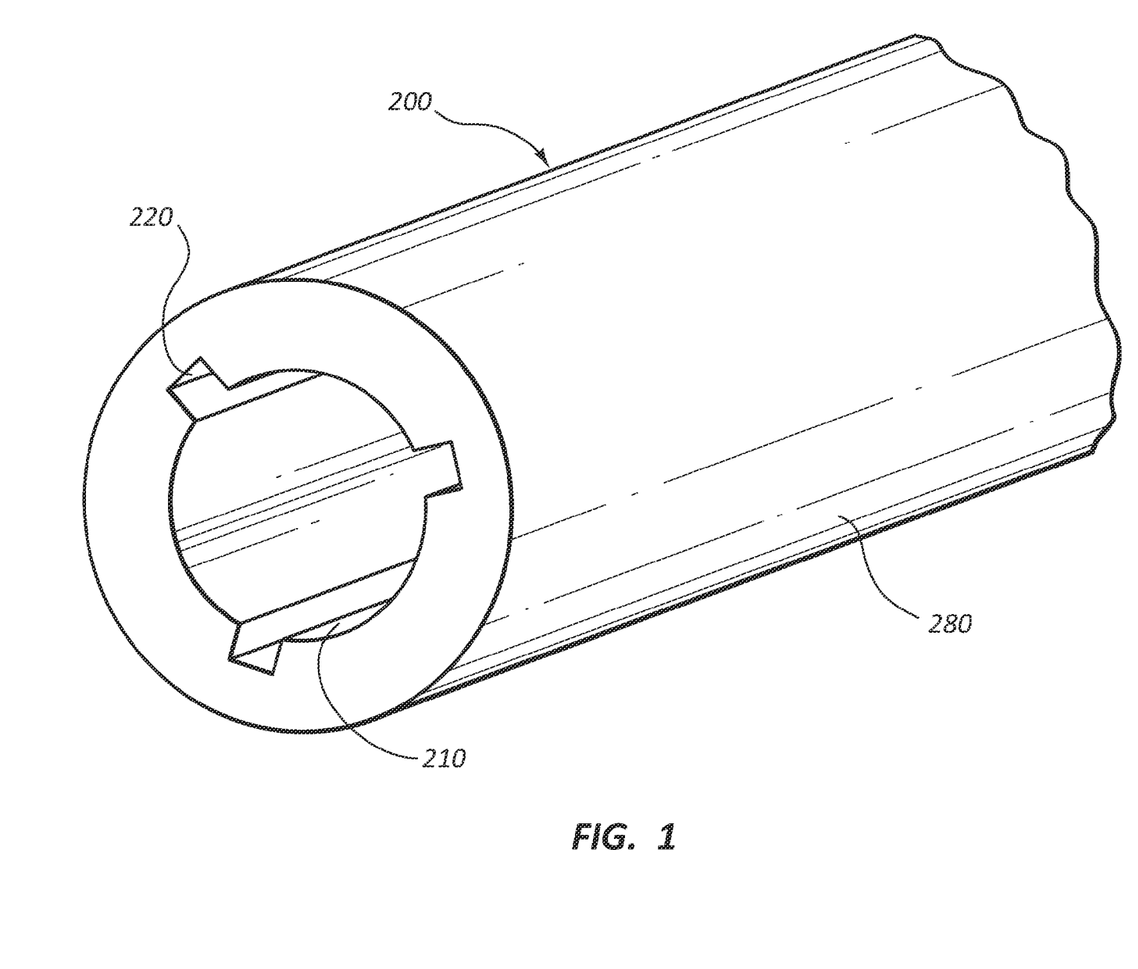
FIG. 1 is a perspective view of the outer tube that constrains the therapeutic medical appliance by radial compression, the tube shown with grooves for receiving the tracks that permit the device to contain a plurality of therapeutic medical appliance while only allowing one stent to be deployed at a time.

Referring generally to the figures where like numerals refer to like parts, varying embodiments of a reusable delivery system, a multifire delivery system and a therapeutic medical appliance are shown. Specifically, referring to FIG. 1, the outer tubular member 200 (alternatively known as an outer sheath) is provided with recesses 220 (alternatively known as grooves) for operatively receiving tracks 300 therein. The outer sheath 200 is certain embodiments can participate in the constraining of the therapeutic medical appliance 100. This is particularly relevant in cases where the therapeutic medical appliance 100 comprises a memory alloy. The outer sheath 200 has both an interior surface 210 and an exterior surface 280, wherein the groove 220 is formed in the inner surface 210 of the outer sheath 200 and runs longitudinally along a portion thereof.

Figure 2:
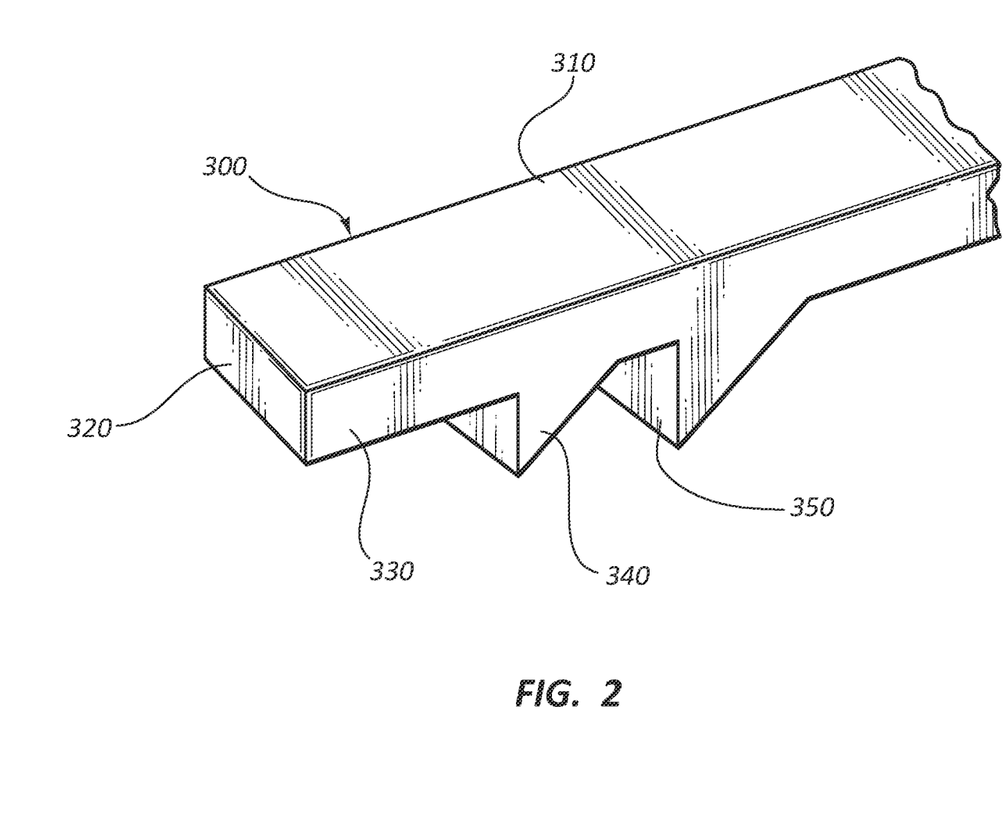
FIG. 2 shows the tracks that ride in the grooves of the outer sheath of FIG. 1, wherein the grooves preferably have unidirectional members that permits the device to deploy a single therapeutic medical appliance and reload multiple times within one procedure.
Figure 3:
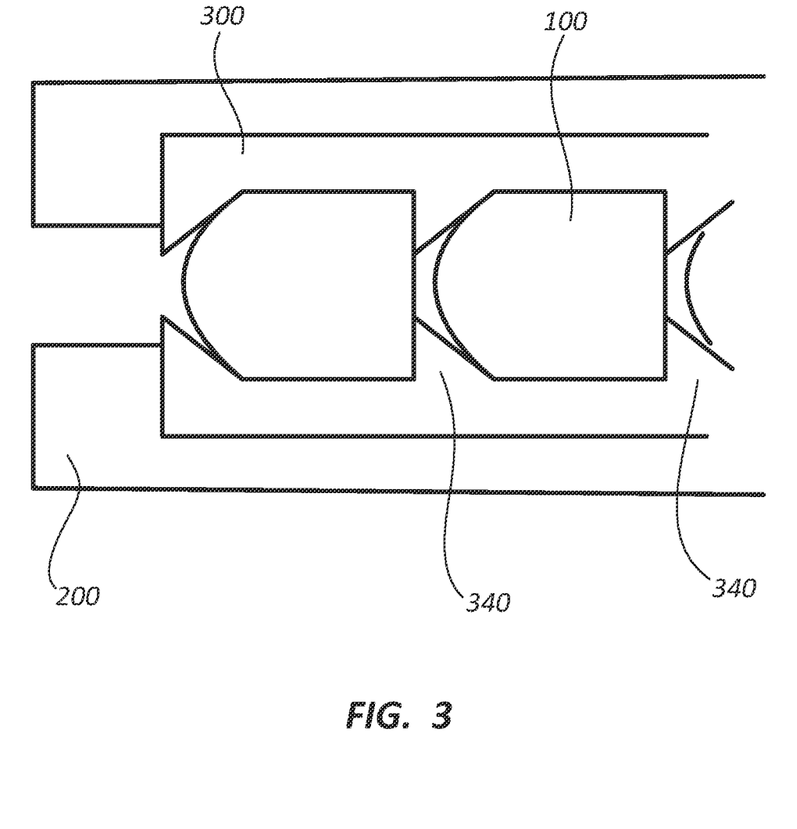
FIG. 3 shows a plurality of therapeutic medical appliances and the relative location of at least two tracks with respect to the therapeutic medical appliances.
Figure 4:
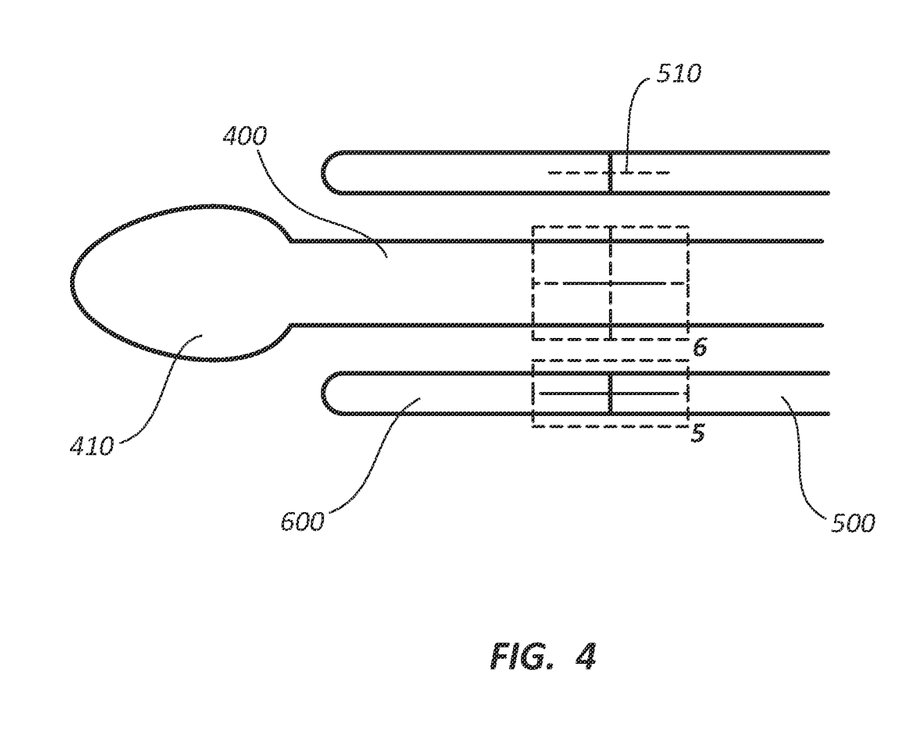
FIG. 4 shows an embodiment of a reloadable delivery device where the therapeutic medical appliance-containing tip snaps onto the outer tube and/or the inner to form the distal region of the delivery device.
Figure 5:
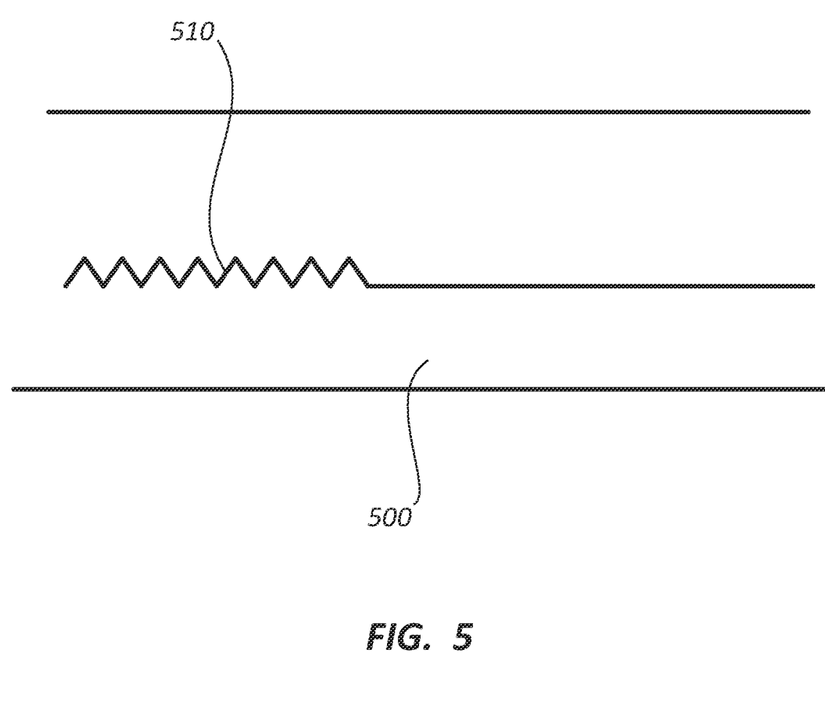
FIG. 5 shows an alternative embodiment of the reloadable delivery device of FIG. 4 where the therapeutic medical appliance-containing tip snaps onto the outer tube and/or the inner to form the distal region of the delivery device.
Figure 6:
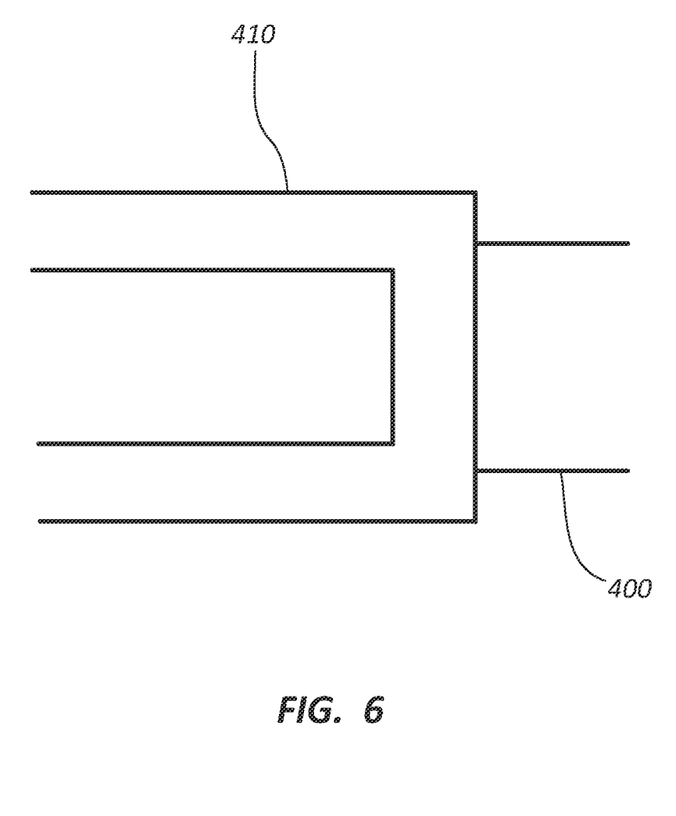
FIG. 6 shows an alternative embodiment of a reloadable delivery device where the therapeutic medical appliance-containing tip has a friction fit coupling with the outer tube and/or the inner to form the distal region of the delivery device.
Figure 7:
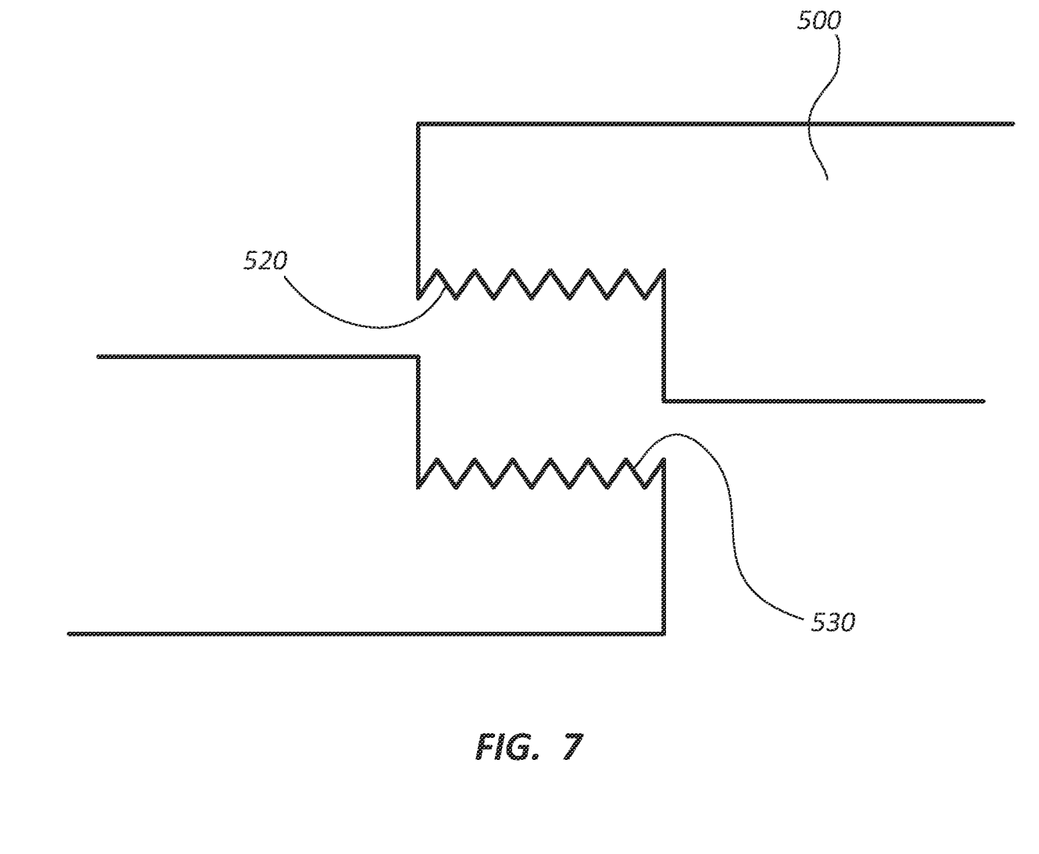
FIG. 7 shows an alternative embodiment of a reloadable delivery device showing the threading components of the reloadable tip.

As shown in FIG. 2, track 300 is operably coupled with groove 220 so as to be slidable therein. The track 300 has a distal end 320, first and second sides 330 and 360. Track 300 also has a top surface 310 that is adjacent groove 220 when in an operable configuration. In certain embodiments, first side 330 and/or second side 360 are in operable communication with groove 220 as well. Moreover, track 300 in preferred embodiments is configured with extensions 340 that preferably have unidirectional faces 350 that are adjacent the proximal region 130 of the therapeutic medical appliance 100 so as to assist with deployment of the therapeutic medical appliance 100 distally without allowing it to move proximally with respect to other therapeutic medical appliances. In preferred embodiments, multiple unidirectional surface containing members 340 are provided to allow for the housing of multiple therapeutic medical appliances 100 in the outer sheath 200. The outer sheath 200 may be configured to have one or more grooves 220 so as to receive one or more tracks 300. As shown in FIG. 3, the therapeutic medical appliance 100 is housed in between the outer sheath 200 directly or indirectly in the event that multiple tracks 300 are provided.

FIGS. 4-7 show an alternative embodiment of a delivery system in accordance with preferred embodiments of the present invention wherein the system is reusable. In particular, an outer sheath 500 is provided that can be separated at junction 510. Junction 510 may comprise a coupling mechanism such as a snap, tension, screw or alternative mating. Shown in more detail in FIGS. 5 & 7 the distal end of the device may be separated from the proximal section. The distal region preferably comprises the section distal the proximal end of the stent, though the distal region may comprise more or less of the outer sheath 500. In embodiments that have an inner sheath 400, the inner sheath may also be removed at a junction similar to that found in the outer sheath 400. In such embodiments the region from the distal tip 410 to a predetermined point on the inner sheath 400 may be removed. The coupling of both the inner and the outer sheath can be accomplished by a variety of coupling means such as those listed above or that may be customary in the fastening art, even though they may not be obvious to use in medical devices prior to exposure to this disclosure.

Figure 8:
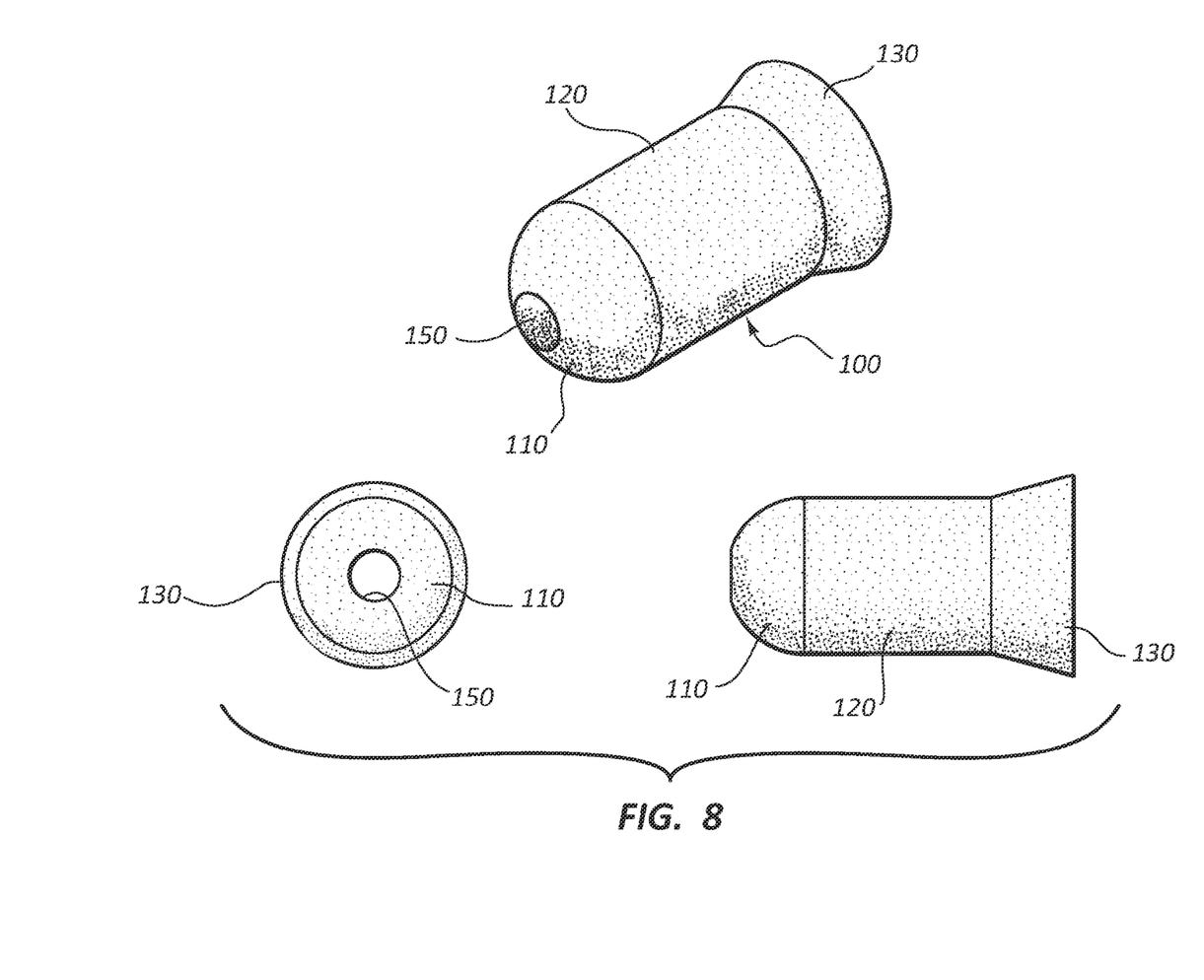
FIG. 8 provides perspective views of the therapeutic medical appliance that does not have a self-sealing membrane at the distal tip.

Referring now to FIG. 8, a preferred therapeutic medical appliance 100 provides a device having a distal end, 110, a medial region 120 and a proximal end 130. Moreover, in certain embodiments, a self-healing membrane 150 is provided that allows for the penetration thereof without permanently damaging the membrane 150. It is also envisioned in certain embodiments that the therapeutic medical appliance may be configured from a bioabsorbable material compatible with mammalian tissue such as a polyglycol.

It should be kept in mind that the handle may be coupled with a portion of the outer sheath or other portions of the delivery system such as the tracks, inner sheath, etc. Moreover, in the reusable embodiments, the distal portion may be disposable or reloadable for reuse provided both the distal and the proximal portions of the device are sterilized before subsequent use.

In practice the therapeutic medical appliance and delivery device may be used to treat various defects, including but not limited to defects characterized by pulmonary blebs and/or diffused destructive parenchymal disease in a patient, by providing one or more therapeutic medical appliances and placing them about a target site in a lung of a patient generally and the segmental airway in particular. Either independently or through utility channels in the outer tube of the delivery device, an adhesive can be introduced by a syringe into the lung through the self-sealing membrane of the therapeutic medical appliance. An adhesive, which is preferably a localized inflammatory response causing and gas-absorbing agent, causes surfaces of lung sections to coalesce and seal the defect. Subsequently, the lung sections are collapsed by evacuating the inflammatory response causing and gas-absorbing agent.

The therapeutic medical appliance may be a simple formed of any number of materials, including but not limited to a shape memory alloy, polymer, elastomer, etc. The self-sealing membrane is not required.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

Figure 9:
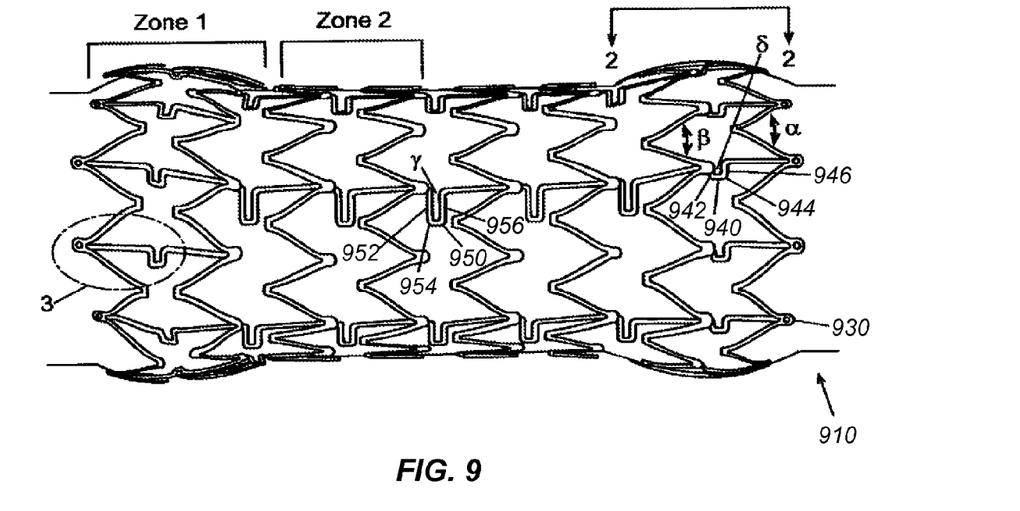
FIG. 9 shows a side perspective view of an exemplary stent in accordance with the present invention.
Figure 10:
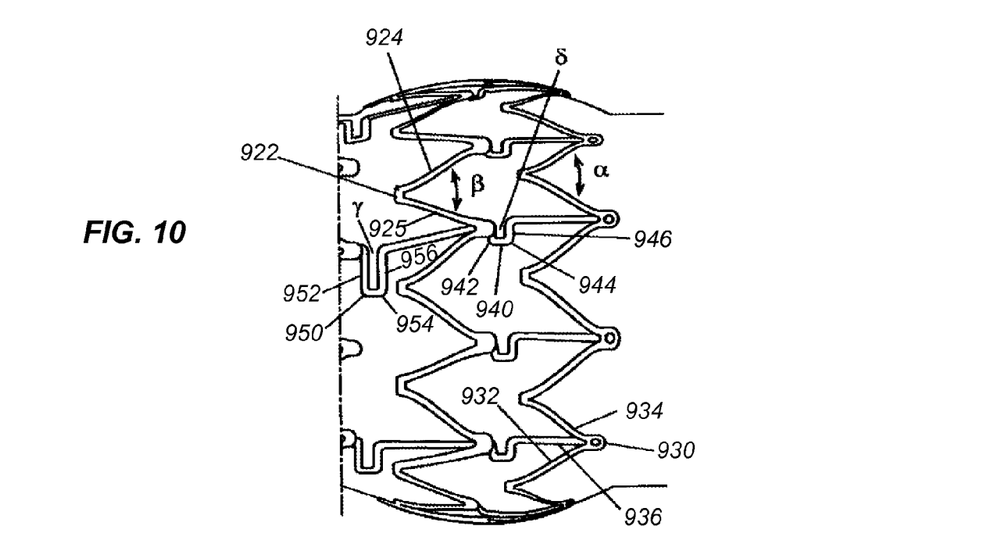
FIG. 10 shows a side perspective view of a single zone of the stent shown in FIG. 9.
Figure 11:
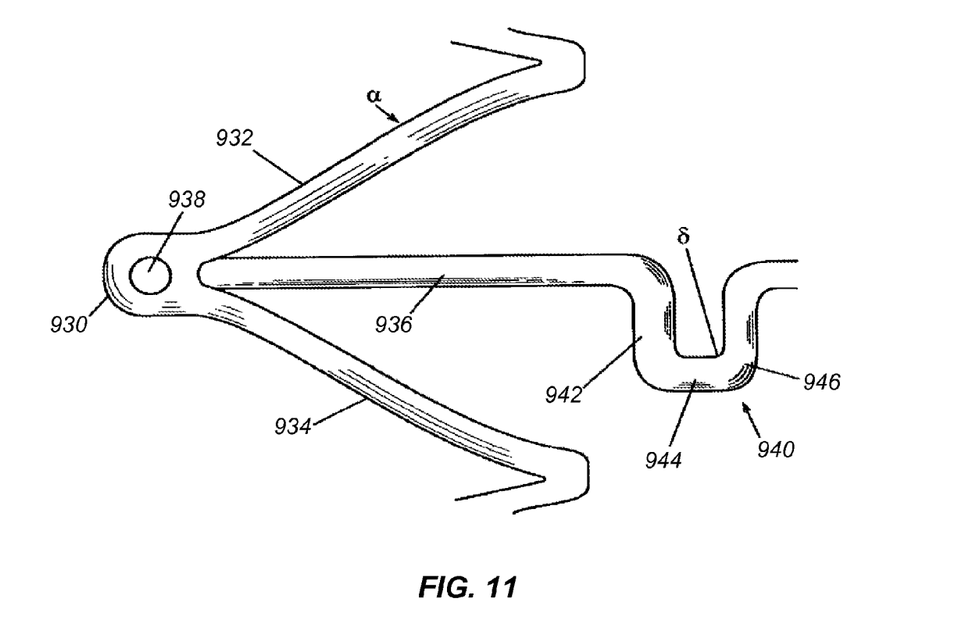
FIG. 11 shows an enlarged perspective view of the interstices of an exemplary zone as shown in FIG. 10.
Figure 12:
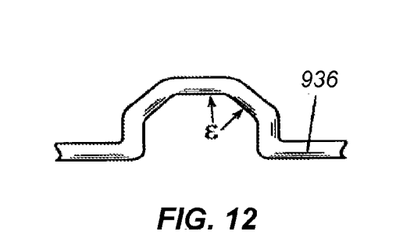
FIG. 12 shows an enlarged perspective view of the interstices of an exemplary zone as shown in FIG. 10 showing an alternative octagonal connection member.
Figure 13:
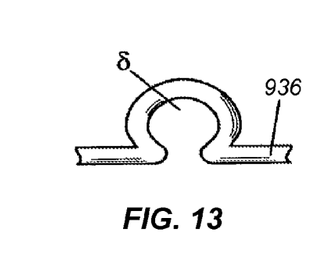
FIG. 13 shows an enlarged perspective view of the interstices of an exemplary zone as shown in FIG. 10 showing an alternative omega shaped connection member.
Figure 14:
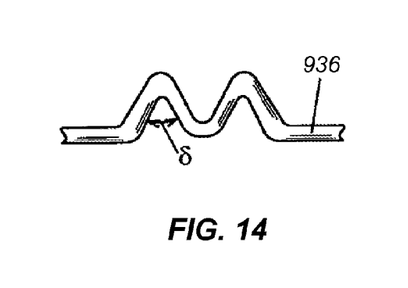
FIG. 14 shows an enlarged perspective view of the interstices of an exemplary zone as shown in FIG. 10 showing an alternative M shaped connection member.
Figure 15:
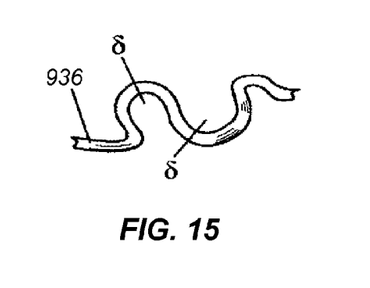
FIG. 15 shows an enlarged perspective view of the interstices of an exemplary zone as shown in FIG. 10 showing an alternative S shaped connection member.

Exemplary stents 910 in accordance with the present invention are shown in FIGS. 9-11 including the preferred interstice geometry. Shown in FIGS. 12-15 are a wide variety of connector geometries that are acceptable, namely, U, V, W, Z, and S geometries to name a few.

In a standard orientation, as shown particularly in FIG. 9, the substantially U-shape connector 950 comprises preferably two leg members 952 & 956 and a crossing member 954 that connects with and extends perpendicularly at preferably 90° angles with respect to the leg members 952 & 956. It must be noted that alternative angles may be provided without departing materially from the invention. The present inventors discovered that if you modify the length of the crossing member 954 and/or the leg members 952 & 956 and/or the angle $\gamma$ at which the crossing member 954 and the leg members 952 & 956 intersect, the relative hardness/softness, radial force and/or flexibility of the stent 910 could be modified. The angles $\gamma$ can be modified at varying acute angles short of 90° or varying obtuse angles greater than 90°. The incremental changes correspondingly change certain characteristics of the stent 910. As a result, different zones of the stent 910 can be given different rigidities to improve patient comfort and for example, in airway stents, to facilitate luminal patency. Moreover, various anatomical lumens may need different degrees of stent rigidity. As a result, stents 910 in accordance with the present invention can be manufactured to exacting specifications to contour properly to various lumens in a patient's anatomy, which may need varying levels of structural support from the medical appliance.

By adjusting the distance between the connector 950 and the zones between which connector 950 resides, the way in which the stent reacts to strain can be modified. By way of non-limiting example, if the connector 950 is oriented closer to one zone than another, the stent will be less flexible and be able to withstand greater radial force. Alternatively, if the connector is equidistant between two zones, the stent will be more flexible and be able to withstand less radial force. Please note that these differences are relative to a neutrally located connector 950. The behavior is a function of distance and as a result varies along a continuum with respect to the connector's orientation between the medium between zones and the tip of each zone. Moreover, within by varying the number of connectors 950 that connect the zones to one another, functionality can be impacted. In particular, the fewer the number of connectors connecting the zones the more torsional flexibility the stent will have. The converse will generally hold true with respect to a greater number of connectors.

Referring now to FIG. 10, stent 910 is shown having several bands within a zone forming substantially arrow shaped regions. In particular, each arrow shaped band preferably comprises a forward angle $\beta$ and a rear angle $\alpha$. The forward angle $\beta$ is formed by the intersection of two legs 924 & 925. Legs 924 & 925 connect at first ends to form the head 922 of angle $\beta$. Second ends of legs 924 & 925 terminate at connectors 940. Connector 940 connects the legs 924 & 925 of forward angle $\beta$ to the legs 932 & 934 of rear angle $\alpha$ via intermediary leg 936. Where legs 932, 934 & 936 connect is the head 930, which defines an aperture 938 for installing suture.

Connector 940, which serves a similar purpose as connector 950 also has a crossing member 944 that connects leg members 942 & 946 at a predetermined angle $\delta$. As discussed above, since form follows function for stents prepared through this novel method, by changing the degrees of angles $\alpha$, $\beta$, $\delta$ & $\gamma$, stent characteristics can be modified. Moreover, by changing the leg lengths of all the previously discussed legs or individual legs separately, additional stent characteristics can be obtained. The beauty of this system is that the desired characteristics can be determined prior to forming the stent and by staying within certain forming parameters, the stent can be formed, crimped, delivered and deployed with confidence that the desired functionality with result. This is important in light of the fact that both vascular and nonvascular lumen have unique topography. As a result, methods and devices in accordance with the present invention usher in the ability to tailor prosthesis to anatomical tissue in general and particular patient anatomy in particular.

The U shaped connectors 940 & 950 have a crossing member and at least two leg members, respectively. The present inventors discovered that if you increase/decrease the length of leg members and/or increase/decrease the length of crossing members and/or vary the angle at which crossing members and leg members intersect, you affect the functionality of the stent. In particular, the shorter the length of the leg members, the less flexibility available in that portion of the stent. Taking particular note of FIG. 11, by way of example only, if you want to decrease the amount of torsional flexibility of the stent 910, you would have to modify the connector 940 so that the legs 942 & 946 are longer than shown and that the angle $\delta$ formed by legs 942 & 946 and crossing member 944, respectively, is slightly greater than 90°. Alternatively, the length of the crossing member 944 can impact the functionality of the stent as well. The stent can be made more rigid by shortening crossing member 944 or the stent may be made more flexible by lengthening crossing member 944. It should be noted that the combination of the changes of leg lengths, crossing member lengths, angle variations, shapes and number of connectors provide the stent with the ability to conform to specific lumens in the anatomy of a patient. The result is a form fitting medical prosthesis that may be tailored to specific anatomical lumens in general and to the anatomical lumens of an individual patient in particular.

In a preferred embodiment, the modification of interstice geometries and manipulation of the U shaped connection member to achieve variable stent functionality is provided. The rigidity of the stent scaffolding or interstice matrix along with the torsionality of the stent itself is principally a function of these modifications. In an exemplary embodiment, the stents relative flexibility can be rated soft, medium or hard based on the degree of flex and torsionality. The less torsionality and flex in the stent the harder the stent is rated.

An exemplary stent in accordance with the present invention with relatively great torsionality and radial flexibility would be rated soft. An exemplary soft rated stent comprises distance between U shaped connectors of about 4.5 µm in the compressed state (i.e., contracted in the 3 mm tube subject to laser etching). Moreover, the length of the crossing member is preferably about 1.0 µm. The lengths of the leg members are preferably about 1.5 µm in length. Additionally the leg members may further comprise feet that attached to the remainder of the stent scaffolding. The feet can be adjusted from a standard length of about 0.25 µm to further adjust the characteristics of the stent. There is additionally a substantially rectangular member incorporated in the U shaped connector with similar capacity for variability. The variability factors and results of modifying the dimensions of the substantially rectangular members are similar to those evinced by leg length dimensional modifications.

By way of example, but not to be construed in any way as limiting, the softness index or relative flexibility can be increased by increasing the various lengths discussed above. For example, by increasing the length of the legs and crossing members of the U shaped connector, flexibility increases. However, with respect to the distance between U shaped members and distance between interstices in a preferred stent embodiment, there is an inverse correlation between length and softness. This relative softness/hardness indexing as a corollary of interstice dimensions is a novel aspect of preferred embodiment of the present invention. As a practical rule of thumb, longer leg lengths coupled with acute angles provide for greater flexibility. Conversely, shorter leg lengths and more obtuse angles provide more rigidity. By way of non-limiting example, a U shaped connector with short legs deviating from the crossing member at angles greater than 90°, will be extremely rigid and resistant to torsional strain as compared to a U shaped connector with longer legs diverging from the crossing member at angles less than 90°.

The invention claimed is:

1. A therapeutic medical appliance for introduction into a cavity in the anatomy of a patient, the medical appliance comprising a tube with distal and proximal ends and the tube defining a cavity extending between the distal and proximal ends, and a first self-sealing membrane disposed in the distal end,
wherein the distal end comprises a convex surface arcuately tapered towards a distal tip and defining a distal tip diameter, wherein a medial region between the distal and proximal ends comprises a substantially uniform medial diameter larger than the distal tip diameter, and wherein the proximal end comprises a flared surface with a flare diameter larger than the medial diameter.

2. The therapeutic medical appliance of claim 1, wherein tube forms a scaffolding such that when pressure is exerted along varying points of the extension of the appliance, the appliance does not undesirably foreshorten or elongate.

3. The therapeutic medical appliance of claim 2, wherein the scaffolding comprises a plurality of circumferential bands connected by a connector, and wherein along the extension of the appliance, the scaffolding forms geometrical interstices.

4. The therapeutic medical appliance of claim 3, wherein the dimensions of the scaffolding geometry determine torsionality of the medical appliance.

5. The therapeutic medical appliance of claim 3, wherein the scaffolding is formed of a memory capable alloy.

6. The therapeutic medical appliance of claim 5, wherein the scaffolding is electropolished.

7. The therapeutic medical appliance of claim 3, wherein the connector comprises a crossing member and a plurality of leg members extending from the crossing member.

8. The therapeutic medical appliance of claim 7, wherein the connector further comprises a rectangular detent extending from a leg thereof.

9. The therapeutic medical appliance of claim 7, wherein the length of the leg members and the degree of the angle at which the legs extend from the crossing member determines the relative flexibility of the medical appliance.

10. The therapeutic medical appliance of claim 9, wherein the angle at which the leg members extend from the crossing member is greater than 90°.

11. The therapeutic medical appliance of claim 10, wherein the medical appliance is relatively rigid.

12. The therapeutic medical appliance of claim 11, wherein the medical appliance is relatively flexible.

13. The therapeutic medical appliance of claim 10, wherein the angle at which the leg members extend from the crossing member is 90° or less.

14. The therapeutic medical appliance of claim 3, wherein the connector is substantially U-shaped.

15. The therapeutic medical appliance of claim 3, wherein the connector is substantially W-shaped.

16. The therapeutic medical appliance of claim 3, wherein the connector is substantially V-shaped.

17. The therapeutic medical appliance of claim 3, wherein the connector is substantially Z-shaped.

18. The therapeutic medical appliance of claim 3, wherein the connector is substantially S-shaped.

19. The therapeutic medical appliance of claim 2, wherein the scaffolding further comprises a coating coupled with the scaffolding, the coating of sufficient thickness to prevent the medical appliance from becoming epithelialized when installed in the desired portion of the patient's anatomy.

20. The therapeutic medical appliance of claim 19, wherein the coating does not inhibit flexing or radial expansion of the medical appliance.

21. The therapeutic medical appliance of claim 20, wherein the coating is coupled with the medical appliance about the first and second ends thereof.

22. The therapeutic medical appliance of claim 1, further comprising a second self-sealing membrane about the proximal end thereof.

23. A method of treating a defect characterized by pulmonary blebs and/or diffused destructive parenchymal disease in a patient, the method comprising the steps of:
providing a therapeutic medical appliance comprising: a tube with distal and proximal ends and the tube defining a void extending between the distal and proximal ends, the medical appliance further comprising a self healing membrane coupled with the distal end thereof, wherein the distal end comprises a tapered, arcuate, convex surface, wherein a medial region between the distal and proximal ends comprises a substantially uniform medial diameter, and wherein the proximal end comprises a flared surface with a flare diameter larger than the medial diameter;
placing the therapeutic medical appliance about a target site in a lung of a patient; and
introducing an adhesive into the lung through the self sealing membrane;
whereby the adhesive causes surfaces of lung sections to coalesce and seal the defect.

24. The method of claim 23, wherein the adhesive is a localized inflammatory response causing and gas-absorbing agent.

25. The method of claim 24, further comprising the step of collapsing sections of the lung by evacuating the inflammatory response causing and gas-absorbing agent.

26. The method of claim 23, wherein the medical appliance further comprises anti-microbial agents coupled therewith.

27. The method of claim 23, wherein the medical appliance further comprises chemotherapeutic agents coupled therewith.

28. A kit for treating a defect characterized by pulmonary blebs and/or diffused destructive parenchymal disease in a patient, the kit comprising:
at least one therapeutic medical appliance comprising: a tube with distal and proximal ends and the tube defining a void extending between the distal and proximal ends, the medical appliance further comprising a self healing membrane coupled with the distal end thereof, wherein the distal end comprises a tapered, arcuate, convex surface, wherein a medial region between the distal and proximal ends comprises a substantially uniform medial diameter, and wherein the proximal end comprises a flared surface with a flare diameter larger than the medial diameter; and a delivery device for delivery of the therapeutic medical appliance(s), wherein the delivery device is capable of placement of a plurality of therapeutic medical appliances in a single procedure.

29. The kit of claim 28, wherein the plurality of therapeutic medical appliances are contained in a single housing.

30. The kit of claim 29, wherein the delivery device can be reloaded with additional housings of therapeutic medical appliances in order to perform multiple procedures.

31. A therapeutic medical appliance for introduction into a cavity in the anatomy of a patient, the medical appliance comprising a tube with first and second ends and the tube defining a cavity extending between the first and second ends, the medical appliance further comprising a self-sealing membrane coupled about the first end thereof, wherein the tube forms a scaffolding, the scaffolding configured to prevent the appliance from undesirably foreshortening or elongating when pressure is exerted along varying points of the longitudinal extension of the appliance, wherein the scaffolding comprises a plurality of circumferential bands connected by one or more connectors, wherein along the longitudinal extension of the appliance, the scaffolding form geometrical interstices, wherein the first end comprises a convex surface arcuately tapered towards a first tip and defining a first tip diameter, wherein a medial region between the first and second ends comprises a substantially uniform medial diameter larger than the first tip diameter, and wherein the second end comprises a flared surface with a flare diameter larger than the medial diameter.

* * * * *